US008852287B2

United States Patent
Kraus et al.

(10) Patent No.: US 8,852,287 B2
(45) Date of Patent: Oct. 7, 2014

(54) FEMORAL HEAD CAP IMPLANT INCLUDING A DEVICE FOR ELECTRICALLY STIMULATING TISSUE

(75) Inventors: Werner Kraus, Munich (DE); Christian Kraus-Von Wesendonk, Munich (DE); Heribert Stephan, Munich (DE)

(73) Assignee: Neue Magnetodyn G.m.b.H, Munich (DE)

( * ) Notice: Subject to any disclaimer, the term of this patent is extended or adjusted under 35 U.S.C. 154(b) by 1775 days.

(21) Appl. No.: 11/125,797

(22) Filed: May 10, 2005

(65) Prior Publication Data

US 2005/0256586 A1 Nov. 17, 2005

(30) Foreign Application Priority Data

May 14, 2004 (DE) .......................... 10 2004 024 473

(51) Int. Cl.
| | |
|---|---|
| *A61F 2/32* | (2006.01) |
| *A61N 1/05* | (2006.01) |
| *A61N 1/32* | (2006.01) |
| *A61F 2/30* | (2006.01) |
| *A61F 2/28* | (2006.01) |
| *A61F 2/36* | (2006.01) |

(52) U.S. Cl.
CPC ....... *A61F 2/3603* (2013.01); *A61F 2230/0069* (2013.01); *A61F 2310/00029* (2013.01); *A61F 2002/30289* (2013.01); *A61F 2002/30975* (2013.01); *A61F 2002/30079* (2013.01); *A61F 2230/005* (2013.01); *A61F 2310/00796* (2013.01); *A61F 2002/30604* (2013.01);

(Continued)

(58) Field of Classification Search
CPC ....... A61N 1/00; A61N 2001/00; A61B 1/00; A61B 17/00; A61B 2010/00; A61B 2217/00; A61B 2218/00; A61F 2/00; A61F 5/00; A61F 9/00; A61F 13/00; A61F 2002/00; A61F 2210/00; A61F 2220/00
USPC .......... 623/23.11, 23.12, 23.14–23.16, 23.49, 623/19.11–19.14, 22.11–22.39
See application file for complete search history.

(56) References Cited

U.S. PATENT DOCUMENTS

| 4,195,367 A | * | 4/1980 | Kraus | ......................... 623/23.49 |
| 4,214,322 A | | 7/1980 | Kraus | .............................. 3/1.91 |

(Continued)

FOREIGN PATENT DOCUMENTS

| DE | 26 11 744 | 9/1977 |
| DE | 3132488 | 2/1983 |

(Continued)

OTHER PUBLICATIONS

F. Lechner, et al. (1981). "Treatment of Pseudarthroses with Electrodynamic Potentials of Low Frequency Range"; Clinical Orthopaedics and Related Research, 161, p. 71-81.

(Continued)

*Primary Examiner* — David Isabella
*Assistant Examiner* — Ann Schillinger
(74) *Attorney, Agent, or Firm* — Nields, Lemack & Frame, LLC

(57) ABSTRACT

In a femoral head cap implant having a cup-shaped cap component and a pin fixed to its concave inner surface, a pick-up coil is arranged in the latter, each respective terminal of the same being connected to a tissue electrode. One tissue electrode comprises a cap component, the other an electrode provided insulated on the pin or on at least one part of the pin which is electrically insulated from the cap component. By inducing a low-frequency alternating current in the pick-up coil by means of an external coil, this low-frequency alternating current flows from the two tissue electrodes through the femoral head bone provided with the implant, thereby promoting the maintenance of its vitality.

16 Claims, 2 Drawing Sheets

Figure 1:
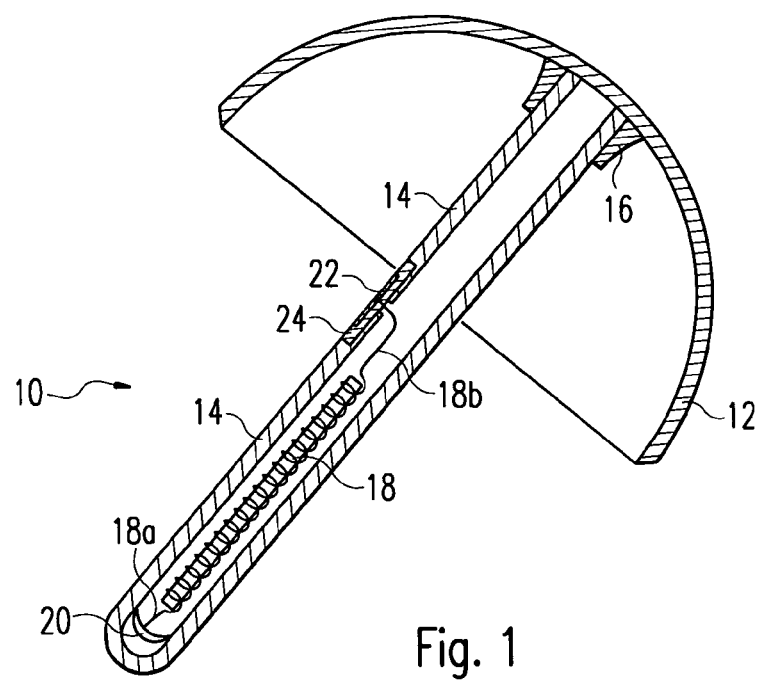

(52) U.S. Cl.
CPC ... *A61F 2/30767* (2013.01); *A61F 2002/30354* (2013.01); *A61F 2002/30878* (2013.01); *A61F 2230/0091* (2013.01); *A61F 2002/30589* (2013.01); *A61N 1/326* (2013.01); *A61F 2002/30568* (2013.01); *A61F 2250/0026* (2013.01); *A61F 2002/30322* (2013.01); *A61F 2002/30462* (2013.01); *A61F 2210/009* (2013.01); *A61F 2002/30593* (2013.01); *A61F 2220/0075* (2013.01); *A61F 2002/2821* (2013.01); *A61F 2002/30171* (2013.01); *A61F 2/3601* (2013.01); *A61F 2310/00179* (2013.01); *A61F 2310/00023* (2013.01); *A61F 2002/30235* (2013.01); *A61F 2220/0033* (2013.01)
USPC ................................. 623/22.15; 607/116

(56) References Cited

U.S. PATENT DOCUMENTS

| | | | | |
|---|---|---|---|---|
| 5,376,122 | A | 12/1994 | Pappas et al. | 623/22.28 |
| 5,383,935 | A | 1/1995 | Shirkhanzadeh | 623/16 |
| 6,034,295 | A * | 3/2000 | Rehberg et al. | 623/23.49 |
| 6,478,824 | B1 | 11/2002 | Hagenmeyer | 623/23.16 |
| 6,503,281 | B1 * | 1/2003 | Mallory | 623/22.15 |
| 6,778,861 | B1 * | 8/2004 | Liebrecht et al. | 607/116 |
| 6,884,264 | B2 * | 4/2005 | Spiegelberg et al. | 623/22.12 |
| 7,172,594 | B2 * | 2/2007 | Biscup | 606/86 A |
| 2003/0014123 | A1 | 1/2003 | Copf et al. | 623/23.14 |
| 2004/0230290 | A1 * | 11/2004 | Weber et al. | 623/1.15 |
| 2005/0256586 | A1 | 11/2005 | Kraus et al. | 623/23.16 |

FOREIGN PATENT DOCUMENTS

| | | | |
|---|---|---|---|
| DE | 3709734 | 10/1988 | |
| DE | 31 32 488 | 6/1990 | |
| DE | 19508753 | 12/1995 | |
| EP | 0 781 532 | 11/1996 | |
| JP | 10-201778 | 8/1998 | |
| WO | WO 01/00097 | * 1/2001 | ............ A61B 17/58 |
| WO | 2004/066851 | 8/2004 | |

OTHER PUBLICATIONS

Ascherl, R. et al. (1985); "Electrical Stimulation of Low Frequency Range in Cases of Pseudarthroses"; Reconstruction Surgery and Traumatology, vol. 19, p. 106-112.
Kraus, W. (1992); "The Treatment of Pathological bone lesion with non-thermal, extremely low frequency electromagnetic fields"; Bioelectrochemistry and Bioenergetics, 27, (1992) p. 321-339.
Kruger T. et al. (2000). "Einfluss der magnetisch induzier-ten Elektrostimulation (MIES) auf die Kallusfestigkeit nach Distraktion der Schafstibia"; Osteologie, 9, p. 157-164.
The European Search Report dated Oct. 27, 2005.
The Chinese communication dated May 9, 2008.
The Japanese communication dated Dec. 9, 2008.
The German communication dated Jan. 26, 2005.

* cited by examiner

FEMORAL HEAD CAP IMPLANT INCLUDING A DEVICE FOR ELECTRICALLY STIMULATING TISSUE

This application claims priority of German Patent Application No. 10 2004 024 473.1 filed on May 14, 2004.

The present invention relates to a femoral head cap implant including a device to electrically stimulate the growth of bone tissue and maintain its vital condition.

It is known that a low-frequency electrical alternating current of a frequency ranging from approximately 8 to 20 Hz can promote tissue growth, in particular bone growth (method pursuant to Kraus-Lechner). The alternating current is applied by at least two tissue electrodes coupled to the terminals of an implanted coil ("pick-up coil"). Comparable to a transformer, the alternating current in the pick-up coil is induced by an external coil, which is in turn fed a low-frequency alternating voltage by a suitable generator (DE-A-31 32 488). The present invention also makes use of this method.

Hip joint shaft prostheses which integrate a pick-up coil and tissue electrodes to stimulate bone growth and prevent loosening are also already known (EP-A-0 781 532).

A brochure from the midland medical technologies company describes a metal-on-metal femoral head cap system developed in association with Derek McMinn FRCS, which does away with the need to replace the entire femoral neck with a prosthesis, but instead has a metal cap placed atop the bone of the hip joint head which has been appropriately excised to receive it. The metal cap is fixed by a pin mounted to its inside implanted in the femoral neck. Such cap prostheses are superior to shaft prostheses in that they effect virtually no discernible change to the geometry of the thigh bone. As studies conducted in the 1980s have shown, however, femoral head bones frequently necrotize under the metal cap within just three to four years, and the metal cap thereby loses its hold. It must then be replaced by a femoral shaft prosthesis with the shaft being anchored in the thigh bone.

Because of the different configurations involved, the stimulation devices known in conjunction with hip prostheses of the type specified above cannot be applied to a femoral head cap system.

The object of the present invention is to provide a femoral head cap system which prevents necrotizing of the bone covered by the metal cap and which maintains bone tissue vitality.

This object is achieved in accordance with the invention by the measures the claims hereto protect as described in the following using examples of embodiments.

The inventive stimulation device is advantageous in that a distribution of current is attained in a femoral head cap system which prevents the necrotizing of the covered bone and preserves bone tissue in its vitality. This thereby solves the problem of the long-term viability of femoral head cap prostheses.

Figure 2:
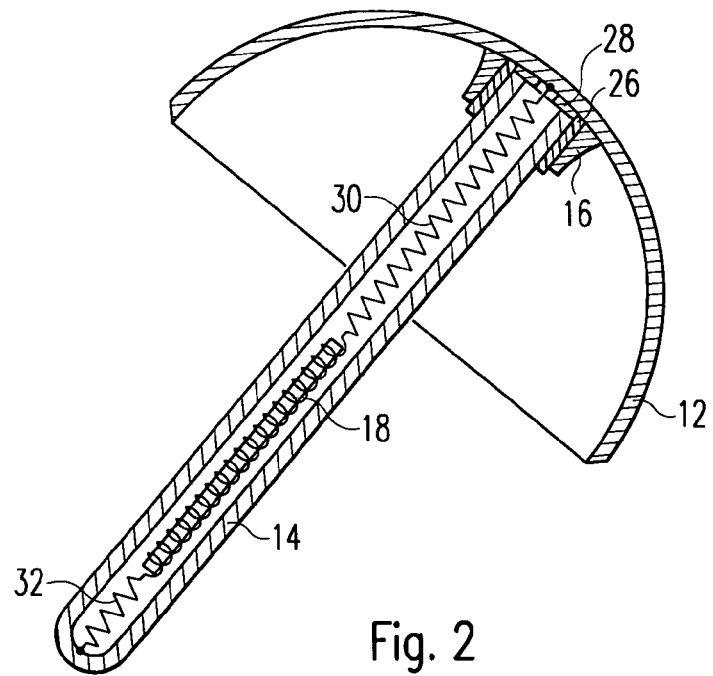
Figure 3:
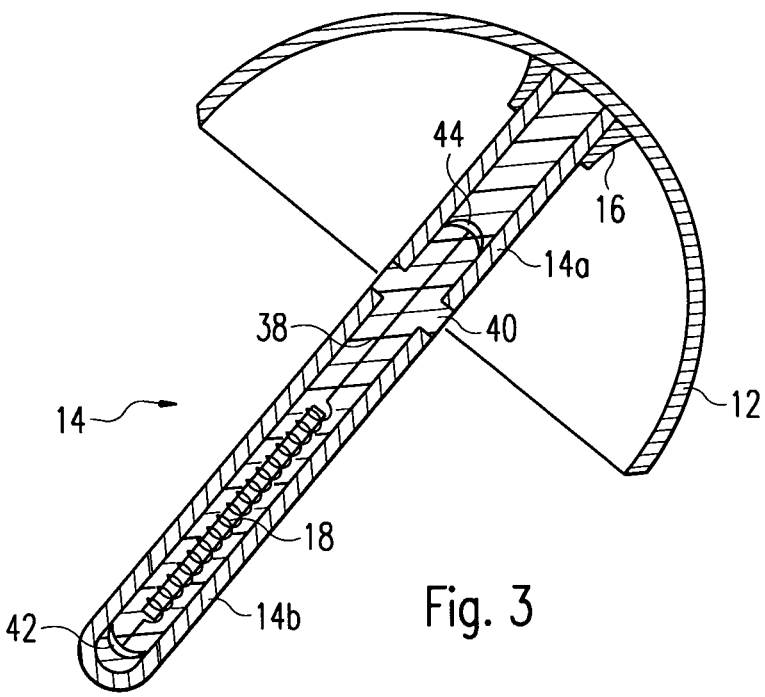
Figure 4:
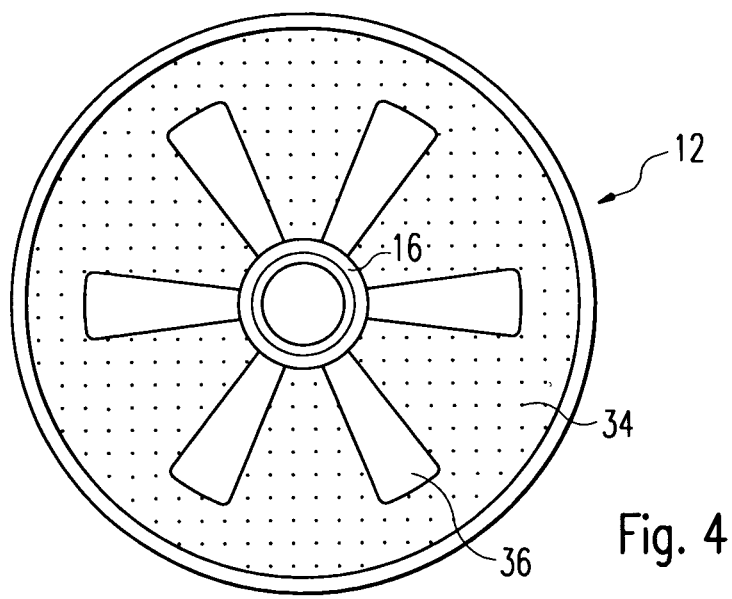

The invention will be described in further detail below with reference to exemplary embodiments in conjunction with the accompanying drawings, which show:

FIG. 1 a sectional view of a femoral head cap implant provided with an electrical stimulation device in accordance with the invention;

FIG. 2 a representation of a second embodiment of the invention corresponding to FIG. 1, FIG. 3 a representation of a third embodiment of the invention corresponding to FIG. 1, and FIG. 4 an enlarged projected representation of the inner surface of a femoral head cap component in accordance with a further embodiment of the invention.

The femoral head cap implant 10 depicted in FIG. 1 comprises a cup-shaped cap component 12 and a rod-like shaft or pin 14. Pin 14 is connected to cap component 12 by a tubular retainer 16 which is affixed to the inner surface of cap component 12 and receives one end of pin 14. Pin 14 is inserted into a hole in the femoral neck bone such that cap component 12 covers the surface of the correspondingly prepared hip joint head.

Cap component 12 and pin 14 are comprised of a tissue-compatible metal, in particular a cobalt-chrome-molybdenum or titanium-aluminum-vanadium alloy. To this extent, the femoral head cap prosthesis is known from the above-cited brochure.

In the embodiment of the invention depicted in FIG. 1, pin 14 is a tube closed at the free end, in which a pick-up coil 18 is accommodated. Pick-up coil 18 exhibits a rod-shaped magnet core and a winding surrounding same, one terminal 18a of which being electrically coupled with the inner wall of the pin by means of a spring 20. Pin 14 and cap component 12 thus form one tissue electrode. The outer surface of pin 14 is provided with a cavity near or within the space enclosed by cap component 12. An outer electrode 22 is disposed in same, insulated from pin 14 by a thin insulating layer 24. A hole is provided in the wall of pin 14 at the location of the cavity. The other terminal 18b of pick-up coil 18 passes insulated through this hole and connects to outer electrode 22. The surface of outer electrode 22 and the edge of insulating layer 24 surrounding it, is flush with the portions of the surface of pin 14 adjacent said cavity such that the outer surface of pin 14 is level. The cavity in which outer electrode 22 is disposed can extend over a portion of the circumference of pin 14 or can ring same. Electrode 22 can be comprised of a vacuum-metallized layer of tissue-compatible metal such as titanium. The insulating layer can be comprised of vacuum-metallized silicon dioxide or another tissue-compatible insulating material. To stimulate growth and maintain the vitality of the bone covered by the cap component and in which the pin is set, a low-frequency alternating current is induced in pick-up coil 18 by means of an external coil (not shown) coupled to an alternating current generator (pursuant the Kraus-Lechner method, see above).

In the embodiment according to FIG. 2, cap component 12 constitutes one tissue electrode and pin 14 constitutes the second tissue electrode. The pin is insulated from tubular retainer 16 by an isolating sleeve 26 which can be comprised of PTFE, for example. An insulating cylindrical disc 28 insulates the face side of pin 14 from the inner surface of cap component 12. The terminals of pick-up coil 18 each are coupled to cap component 12 or pin 14 by means of a pressure spring 30, 32.

The interior of pin 14 of the implants according to FIGS. 1 and 2 is normally filled with insulating sealing compound, in particular tissue-compatible epoxy resin (not depicted in FIGS. 1 and 2).

In the embodiment according to FIG. 3, pin 14 is provided with two members 14a, 14b electrically insulated from one another. Members 14a, 14b are connected by sealing compound 38 which fills pin members 14a, 14b and forms an annular collar 40 between same, the outer surface of which is flush with that of pin members 14a, 14b. Pick-up coil 18 is accommodated in one member 14b of the pin, here the member facing away from the cap component. The one terminal of pick-up coil 18 is coupled to member 14b by means of a spring 42. The other terminal is coupled to member 14a by means of a wire and a spring 44. Pin member 14b thus constitutes one tissue electrode and member 14a with cap component 12 the other tissue electrode. As depicted, the pin's outer member 14b forming the one tissue electrode preferably terminates near the edge of or within the space enclosed by cap component 12 so as to ensure a favorable distribution of current in the portion of the femoral neck bone covered by cap component 12.

The two pin members 14a, 14b can also be connected by means of a short cylindrical spacer, e.g. of ceramic or PTFE, having a collar between the two pin members, the surface of which is flush with the pin members. The one connecting lead of the pick-up coil then runs through said spacer. Such a spacer can be fixed by means of radial dowels in pin members 14a, 14b.

The inner surface of cap component 12 of the embodiment described above can be partly covered by a layer 34 of insulating material, as is indicated by dots in FIG. 4. Said insulating material layer 34 contains or is comprised of hydroxylapatite ($Ca_5[(PO)_4]_3OH$), the main element of solid bone substance. It may also be comprised of vacuum-metallized silicon dioxide or another tissue-compatible insulating material. The insulating coating allows for increasing the current density at the open electrode regions 36 coming into contact with the bone and/or limiting the flow of current to specific ranges.

Should the pin and/or the cap component be made of electrically nonconductive material such as ceramic, conductive material coatings are provided to be the equivalent of the components serving as tissue electrodes in the embodiments described above.

The invention claimed is:

1. A femoral head cap implant having a cap component(12) for covering a diseased hip joint head and having a pin (14) insertable into a femoral neck bone for fixing the cap component atop the hip joint head, whereby the cap component and pin comprise a tissue-compatible metal, characterized in that a pick-up coil (18) having two terminals in which a low-frequency alternating current is inducible is arranged in said pin (14); that one terminal of the pick-up coil is coupled to said cap component(12) and the other to a second tissue electrode (22, 14, 14a) and wherein said cap component comprises a concave surface that covers the surface of said hip joint head and the pin (14) is fixed to the concave inner surface of the cap component (12).

2. The femoral head cap implant according to claim 1, characterized in that said pin comprises two members (14a, 14b) electrically insulated from one another by an insulation, each coupled to one respective terminal of the pick-up coil and serving as tissue electrodes.

3. The femoral head cap implant according to claim 2, characterized in that the insulation comprises sealing compound (38) with which members (14a, 14b) of said pin are filled.

4. The femoral head cap implant according to claim 2, characterized in that the insulation comprises an insulating spacer which extends into the opposite ends of the pin members and through which passes a terminal of the pick-up coil.

5. The femoral head cap implant according to one of claims 2 through 4, characterized in that one member (14a) of the pin is electrically coupled to said cap component.

6. The femoral head cap implant according to one of claims 2 through 4, characterized in that the insulation comprises an annular collar (40), the surface of which is flush with pin members (14a, 14b).

7. The femoral head cap implant according to one of claim 1, 2, 3 or 4, characterized in that a portion of the inner surface of cap component (12) is provided with an insulating layer (34).

8. The femoral head cap implant according to claim 7, characterized in that said insulating layer (34) comprises hydroxylapatite.

9. The femoral head cap of claim 2, wherein said second electrode terminates near the edge of or within the space enclosed by said cap component so as to ensure a favorable distribution of current in the portion of the femoral neck bone covered by said cap component.

10. The femoral head cap implant according to claim 1, characterized in that said pin (14) is fixed to said cap component (12) by a tubular retainer (16) affixed to the inner surface of said cap component (12).

11. A femoral head cap implant, comprising:
a cap component(12), insertable into a femoral neck bone, comprising a concave surface that covers the surface of a hip joint head, and
a pin (14) fixed to and extending from said concave surface into said femoral neck bone,
whereby said cap component and said pin comprise tissue-compatible metals, and wherein a pick-up coil (18) having two terminals in which a low-frequency alternating current is inducible is arranged in said pin (14) such that one terminal of the pick-up coil is coupled to said cap component(12) and the other terminal to a second tissue electrode (22, 14, 14a).

12. The femoral head cap implant of claim 11, wherein said pin is electrically insulated from said cap component and said second tissue electrode comprises said pin.

13. The femoral head cap implant of claim 11, wherein said pin is electrically coupled to said cap component and comprises a cavity near or within the space enclosed by cap component, and said second tissue electrode is disposed in said cavity.

14. A femoral head cap implant, comprising:
a pick-up coil (18) having two terminals in which a low-frequency alternating current may be induced,
a cap component(12) comprising one of said terminals and having a concave surface that covers the surface of a hip joint head, and
a pin (14) fixed to and extending from said concave surface, comprising a second tissue electrode (22, 14, 14a) coupled to the second of said terminals.

15. The femoral head cap implant of claim 14, wherein said pin is electrically insulated from said cap component and said second tissue electrode comprises said pin.

16. The femoral head cap implant of claim 14, wherein said pin is electrically coupled to said cap component and comprises a cavity near or within the space enclosed by cap component 12, and said second tissue electrode is disposed in said cavity.

* * * * *